United States Patent [19]

Farquhar

[11] Patent Number: 4,968,788

[45] Date of Patent: * Nov. 6, 1990

[54] BIOLOGICALLY REVERSIBLE PHOSPHATE AND PHOSPHONATE PROTECTIVE GRUOPS

[75] Inventor: David Farquhar, Houston, Tex.

[73] Assignee: Board of Regents, The University of Texas System, Austin, Tex.

[*] Notice: The portion of the term of this patent subsequent to Mar. 28, 2006 has been disclaimed.

[21] Appl. No.: 300,264

[22] Filed: Jan. 23, 1989

Related U.S. Application Data

[63] Continuation-in-part of Ser. No. 848,741, Apr. 4, 1986, Pat. No. 4,816,570, which is a continuation-in-part of Ser. No. 445,653, Nov. 30, 1982, abandoned.

[51] Int. Cl.$^5$ .............................................. C07H 19/00
[52] U.S. Cl. ........................................ 536/27; 536/28; 536/29
[58] Field of Search ........................ 536/23, 27, 28, 29

[56] References Cited

U.S. PATENT DOCUMENTS 4,711,955 12/1987 Ward et al. ............................ 536/23
4,816,570 3/1989 Farquhar ................................ 536/27

OTHER PUBLICATIONS

Freed et al., Biochemical Pharmacology, 38:3193-3198 (1989).
Ghyczy et al., Chemical Abstract 101:146138b (1984).
Hunston et al., J. Med. Chem., 27:440-444 (1984).
P. Herdewijn, et al., J. Med. Chem. 30, 1270-8(1987).
T. A. Krenitsky, et al., J. Med. Chem. 26, 891-895 (1983).
K. Kondo et al., J. Med. Chem. 22, 639-646 (1979).
F. Eckstein, Angew. Chem. (Ger.) 77, 912 (1965).
D. E. Gibbs, et al., Some 5'-Azido and 5'-amino-2'-deoxyribunucleosides, Their 3'-phosphates, and Their 3'-phosphoimidazolides, 3, 315-334 (1976).
E. DeClercq, et al., Progress in Medicinal Chemistry, 23, 187-218 (1986).
M. Mansuri, et al., Annual Reviews in Medicinal Chemistry: Antiviral Agents, 22, 139-148 (1987).

*Primary Examiner*—John W. Rollins
*Assistant Examiner*—James O. Wilson
*Attorney, Agent, or Firm*—Arnold, White & Durkee

[57] ABSTRACT

Protective groups are provided which are suitable for masking phosphates and phosphonates. The protected compositions can be introduced in a biological system and then demasked under certain biological conditions. This method permits phosphates and phosphonates which would themselves degrade in the biological system and therefore be ineffective to be introduced in a protected form and late released under the proper conditions.

14 Claims, 1 Drawing Sheet

BIOLOGICALLY REVERSIBLE PHOSPHATE AND PHOSPHONATE PROTECTIVE GRUOPS

BACKGROUND OF THE INVENTION

This patent application is a continuation-in-part of Ser. No. 848,741, filed on Apr. 4, 1986, U.S. Pat. No. 4,816,570 which was a continuation-in-part of Ser. No. 445,653, filed on Nov. 30, 1982, now abandoned. Both of those documents are incorporated here by reference.

This invention relates to the use of biologically reversible protective groups in medicinal chemistry. More particularly, it relates to providing ionic phosphate and phosphonate compounds intracellularly in biological systems through the use of biologically reversible protective groups.

Bioreversible protective groups and their uses are well-known in medicinal chemistry. Some compounds that are potentially useful in biological systems cannot be directly provided in those systems, because they will be rapidly decomposed or are otherwise incompatible with that biological environment in a way that renders them ineffective. However, when this type of compound is derivatized with protective groups, the composite product usually has different physical and chemical properties than the parent. These modified properties can make the product suitable for introduction into certain biological environments that its parent is not. If the protective groups are later removed under biological conditions, the parent compound is left to perform its useful function.

This general method has a number of applications. For example, if the parent is unstable under the relevant biological conditions, it can be derivatized with protective groups which will create a more stable product. The protective groups can be selected so that they will be removed under predetermined biological conditions that exist at the site in the system where the parent is needed.

One area where this concept has apparently not yet been applied with satisfactory results is in the manipulation of phosphate and phosphonate compounds. These compounds, particularly phosphomonoesters and phosphodiesters, play a key role in cellular metabolism. They are involved in almost every metabolic sequence, including the synthesis of carbohydrates, lipids, amino acids, proteins, nucleotides and nucleic acids. One logical way to regulate these metabolic processes is to inhibit intracellular phosphate metabolizing enzymes by using structurally analogous phosphates. These phosphoesters have very substantial therapeutic potential, but thus far they have not been practically useful, because they usually cannot penetrate cell membranes.

There are two reasons for this penetration problem. First, these phosphoesters are negatively charged at physiologic pH and are highly hydrophilic. Consequently, they are chemically incompatible with lipid membranes. Second, most of these compounds are rapidly degraded by enzymes in the blood and on cell surfaces.

As an example, most purine and pyrimidine antimetabolites used in the treatment of cancer require intracellular conversion to the corresponding 5'-mono-, di-, or tri-phosphates in order to exert cytotoxicity. In experimental tumors, resistance to these agents frequently correlates with the deletion or decreased activity of enzymes that convert the administered drugs to the 5'-mononucleotides.

These problems have been recognized since about 1955. A number of attempts have been made to overcome them by using protective groups to change the phosphates into neutral, lipophilic derivatives which could resist the blood and cell surface enzymes. These derivatives would theoretically enter the target cells and then be demasked. This has apparently never been satisfactorily achieved in practice. Prior art masked phosphates have basically proved to be biologically inert. This is believed to be attributable to their failure to demask under biological conditions.

Thus, there remains a need for means to provide useful phosphates and phosphonates intracellularly. For this goal to be achieved through the use of protective groups, the masked phosphate must not be degraded by blood or cell surface enzymes and the protective groups must be removed under the biological conditions that exist in the target cells.

SUMMARY OF THE INVENTION

Bioreversibly protected phosphate or phosphonate compositions in accordance with the present invention use either of two types of protective groups that can be cleared by enzymes known to exist in the body. ("Bioreversibly protected phosphate or phosphonate composition" is used in this specification and the appended claims to refer to a parent phosphate or phosphonate which has been derivatized with a protective group or groups.) When a phosphate is derivatized with the first type of protective group, the protected composition has the formula:

When a phosphonate is derivatized with the first type of protective group, the protected composition has the formula:

$R^1$ can be hydrogen; alkyl, alkaryl, or aryl hydrocarbon, or an organic derivative thereof (e.g., nitroalkyl, haloalkyl, aminoalkyl, carboxyalkyl, nitroaryl, haloaryl, aminoaryl, carboxyaryl, etc.); or amine. $R^1$ is preferably an alkyl, alkaryl, or aryl hydrocarbon having from 1-10 carbon atoms; or an amine having the formula $NR^4R^5$, where $R^4$ and $R^5$ are independently hydrogen or an alkyl hydrocarbon having from 1-10 carbon atoms. $R^1$ is most preferably an alkyl, alkaryl, or aryl hydrocarbon having from 1-6 carbon atoms; or $N(CH_3)_2$.

$R^2$, part of the parent phosphate or phosphonate, can be any organic or inorganic residue, such as a sugar, nucleoside, lipid, amino acid or polypeptide. $R^2$ is preferably hydrogen; an alkyl, alkaryl, aryl or alkoxycarbonyl hydrocarbon; or a nucleoside such as a 2'-deoxynucleoside.

When a phosphate or phosphonate is derivatized with the second type of protective group, the protected composition has the formula:

$R^1$ can be hydrogen, alkyl hydrocarbons having 1–10 carbons, alkaryl or aryl hydrocarbons having 6–10 carbons, or organic derivatives thereof, or amine. When $R^1$ is an amine it preferably has the formula $NR^4R^5$, where $R^4$ and $R^5$ are independently hydrogen or an alkyl hydrocarbon having from 1–10 carbon atoms. $R^1$ is most preferably an alkyl, alkaryl, or aryl hydrocarbon having from 1–6 carbon atoms; or $N(CH_3)_2$. Specific preferred examples are H, $CH_3$, $CH_2CH_3$, $CH(CH_3)_2$, and $C(CH_3)_3$.

$R^3$ is hydrogen or an alkyl hydrocarbon having 1–3 carbons, preferably hydrogen or a methyl group.

$X^1$ is selected from the group consisting of H and $R^1COOCR_2^3$, while $X^2$ is selected from the group consisting of $R^2$ and $OR^2$.

$R^2$, part of the parent phosphate or phosphonate, again can be any organic or inorganic residue, such as a sugar, nucleoside, lipid, amino acid or polypeptide. $R^2$ is preferably selected from the group consisting of hydrogen, alkyl hydrocarbons having 1–10 carbons, aryl and alkaryl hydrocarbons having 6–10 carbons, and nucleosides.

$R^2$ substituents that are particularly useful include uracil 2′,3′-dideoxynucleosides, cytosine 2′,3′-dideoxynucleosides, purine 2′,3′-dideoxynucleosides, and pyrimidine acyclic nucleosides.

Both types of protected compositions are resistant to the blood and cell surface enzymes that degrade the parent phosphates. Furthermore, they both demask under biological conditions, so that at least some of the parent phosphates or phosphonates will be able to perform their desired intracellular functions.

The demasking mechanism is believed to be slightly different for the two types of protected compositions. For the first type, it appears to begin with the degradation of the protected phosphate or phosphonate to an unstable intermediate by carboxylate esterase. Cell-penetration may occur before or after this step. However, once the parent compound is completely demasked, it is once again unable to penetrate cell membranes. The unstable intermediate spontaneously ring opens to form its aldehydo tautomer. Next, the tautomer spontaneously eliminates acrolein, leaving the parent phosphate or phosphonate.

The demasking mechanism for the second type also appears to begin with degradation by carboxylate esterase, this time forming an unstable first intermediate. The first intermediate spontaneously eliminates an aldehyde or ketone to create a second intermediate, which is in turn degraded by carboxylate esterase to form an unstable third intermediate. The third intermediate spontaneously eliminates another aldehyde or ketone, leaving the parent phosphate or phosphonate. As with the first type, cell-penetration can be before or after degradation begins, but must be before the phosphate or phosphonate is completely demasked.

With either type of protective group, some of the protected compositions may break down outside cell membranes. However, at least some of the phosphates or phosphonates should be released within the target cells where they can be used for a variety of purposes.

One species of the second type of protective group, acyloxymethyl radicals, has been used in the past to mask carboxylic acids. However, neither they nor the first type have apparently ever been used in conjunction with phosphates or phosphonates.

The $R^1$ and $R^3$ substituents on these two types of protective groups can be modified to give the masked composition almost any desired physical or chemical property. By thus controlling the properties of the protected composition, variables such as location and rate of demasking can be controlled. This method has potential applications in modulating biochemical pathways, abrogating metabolic deficiencies, circumventing resistance to anticancer drugs and developing new anticancer, antiviral, and antiparasitic drugs.

BRIEF DESCRIPTION OF THE DRAWINGS

In accordance with the present invention.

DETAILED DESCRIPTION OF SPECIFIC EMBODIMENTS

The present invention relates to protective groups that can be used to mask phosphates or phosphonates. The protected composition demasks under biological conditions, thus leaving the parent phosphate or phosphonate available for reaction. This method has potential medical applications with any phosphate or phosphonate which has a therapeutic effect. (As used in this application and the appended claims, "therapeutic effect" means the diagnosis, cure, mitigation, treatment, or prevention of disease in man or other animals, or an effect on the structure or any function of the body of man or other animals.)

Figure 1:
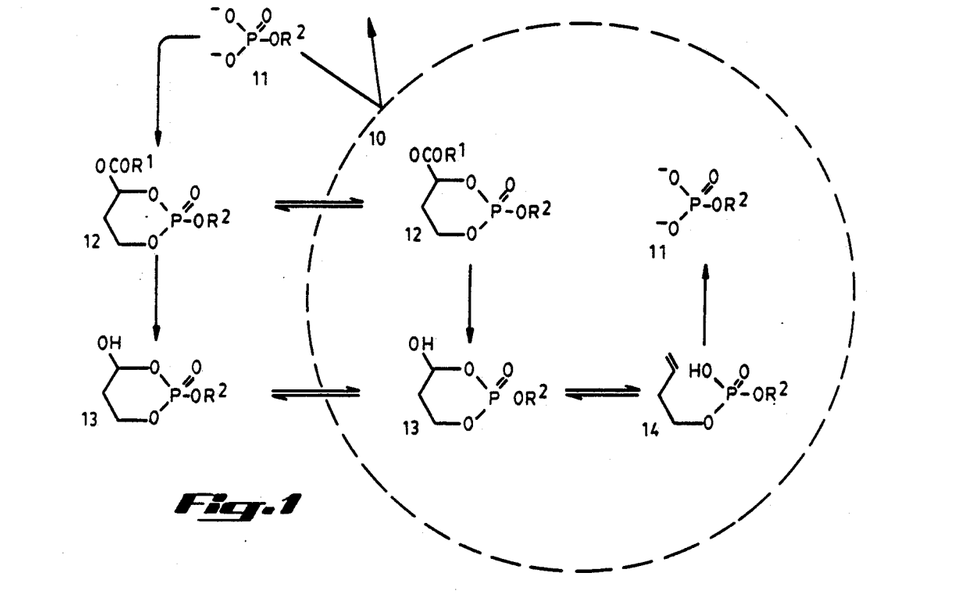
FIG. 1 shows the demasking mechanism believed to occur for the first type of phosphate protective group.

One type of protective group and a method for its use is shown in FIG. 1. A parent phosphate 11 is derivatized with the first type of protective group to form a bioreversibly protected composition 12. The $R^1$ and $R^2$ substituents on this composition can be as previously described.

The protected composition 12 is introduced into a biological system. While the parent phosphate 11 could not penetrate cell membranes 10, the protected composition 12 can. Carboxylate esterase degrades the protected composition 12, either before or after cell penetration, and produces an unstable intermediate 13. The intermediate 13 spontaneously ring opens to form its aldehydo tautomer 14. The tautomer 14 spontaneously eliminates acrolein to give the parent ionic phosphate 11.

The mechanism would be the same for a protected phosphonate.

Figure 2:
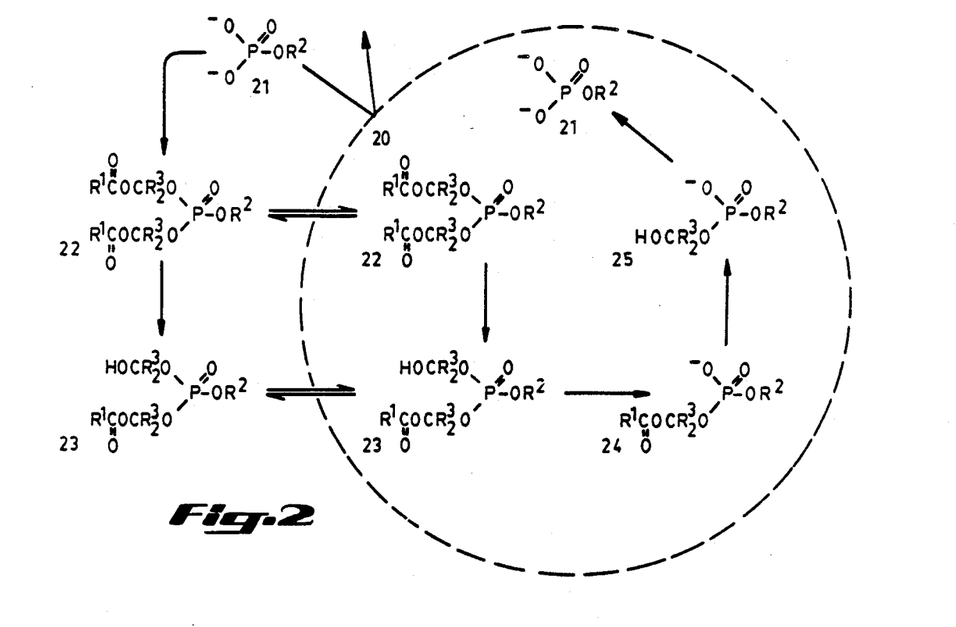
FIG. 2 shows the demasking mechanism believed to occur for the second type of phosphate protective group.

A second type of protective group and its use are shown in FIG. 2. A parent phosphate 21 is derivatized with the second type of protective group to form a protected composition 22. $R^1$, $R^2$, and $R^3$ can be as previously described. The protected composition 22 is capable of penetrating cell membranes 20, and can do so before or after degradation begins.

Carboxylate esterase degrades the protected composition 22 to an unstable first intermediate 23. The first intermediate 23 then spontaneously eliminates an aldehyde or ketone to create a second intermediate 24. Carboxylate esterase degrades the second intermediate 24 to given an unstable third intermediate 25. This substance spontaneously loses an aldehyde or ketone, leaving the parent phosphate 21.

The mechanism would be the same for a protected phosphonate.

Several tests have been performed with both types of protected compositions. These protected compositions have proved to be biologically active, unlike the prior art masked phosphates. The stabilities of these protected compositions were determined in aqueous buffered solutions having pH ranging from 1 to 10, and also under selected biological conditions. Except for the acetoxymethyl derivatives of the second type, these phosphoesters were relatively stable in a neutral environment. They reverted to their parent compounds in acidic or basic media.

The derivatization reaction for both types of protected compositions can be carried out in a number of ways. Several possibilities are described below. Example 1 concerns the first type of protected composition and the remainder of the examples concern the second type.

EXAMPLE 1

A solution of acrolein (6.72 g, 8.01 ml) in anhydrous chloroform (50 ml) was cooled to 5° C. in an ice bath. Dry hydrogen bromide gas was then introduced with stirring until the solution was saturated. Pivaloyl bromide (28.6 g) was added, followed by 0.2 g of zinc chloride, and the reaction mixture was stirred at room temperature for 5 days. The crude reaction product was directly fractionated to yield 16.4 g of 1,3-dibromo-1-pivaloyloxypropane. The boiling point of this product wa 85° C. at 1.5 mm Hg.

Anhydrous sodium iodide (1.24 g, 0.0082 mole) was dissolved in dry acetone (25 ml), and the solution was treated dropwise with stirring under a dry nitrogen atmosphere with a solution of the 1,3-dibromo-1-pivaloyloxypropane (1,00 g, 0.0033 mole) in acetone (3.0 ml). After stirring at ambient temperature for 3 hours, the reaction mixture was poured into dry hexane (150 ml).

Insoluble salts were removed by filtration, under nitrogen, through a bed of diatomaceous earth. The yellow filtrate was concentrated on a rotary evaporator at less than 30° C. The remaining oil was taken up in dry hexane (30 ml) and again filtered to remove some insoluble residue. The solution was concentrated as described above to give 1.40 g of a light yellow oil.

On attempted distillation this product underwent extensive decomposition. Since the IR, NMR and MS of the compound were consistent with the anticipated structure, and since the compound gave satisfactory elemental analytical data, it was used in subsequent reactions without further purification.

Next a solution of the 1,3 diiodo-1-pivaloyloxypropane (1.4 g) in dry ethylene glycol dimethyl ether (10 ml) was added with stirring under a dry nitrogen atmosphere to a solution of bis(tetrabutylammonium)phenyl phosphate (2.17 g, 0.0033 mole) in dry ethylene glycol dimethyl ether (200 ml). (Thus, R$^2$ was C$_6$H$_5$.) The reaction mixture was refluxed for 2 hours and then cooled to room temperature and filtered through a sintered glass funnel.

After removal of solvent on a rotary evaporator at less than 80° C., the residual oil was preadsorbed on drycolumn silica gel (20 g) which was then transferred to a 30"×1" column of the same adsorbent. The column was developed with ethyl acetate-hexane (80/20, v/v). Product bands were located by inspection under UV light (254 nm). The products were eluted from the silica gel with chloroform and further purified by chromatography on two thick-layer silica plates (20 cm×20 cm×2 mm). The products, which were obtained as viscous oils, were shown by MS and NMR to be stereoisomers (arising from the presence of two chiral centers in the molecule at positions 2 and 4). The total yield for the four isomers was 210 mg.

Although the product was stable in organic solvents or aqueous buffers, it was quantitatively converted to phenyl phosphate when treated with strong acids or bases. Similarly, the product reverted to phenyl phosphate when incubated at 37° C. for 30 minutes with mouse plasma.

This synthesis can be summarized as follows:

This procedure was later repeated using bis(tetrabutylammonium) benzyl phosphate, i.e., with the R$^2$ substituent being C$_6$H$_5$CH$_2$.

EXAMPLE 2

A disilver phosphate was obtained from the corresponding disodium salt by reaction with silver nitrate in water. The disilver phosphate was reacted with a 2.5 molar excess of an iodomethyl ester in anhydrous benzene at room temperature for about 5 hours. The product was a bis(acyloxymethyl) phosphate. Several runs of this reaction were performed.

In this run, the $R^2$ substituent of the parent phosphate was $C_6H_5$ and the $R^1$ substituent of the protective group was $CH_3$. The product of this reaction was bis(acetoxymethyl) phenyl phosphate and the yield was 5%.

The protected product was stable in neutral aprotic solvents such as benzene, diethyl ether and ethyl acetate. However, in protonic solvents such as ethanol, water or 0.05M potassium phosphate buffer (pH 7.4), it was slowly converted to mono(acetoxymethyl) phenyl phosphate. The half-life was greater than 4 hours.

These solutions were analyzed by (HPLC) high performance liquid chromatography (Waters model ALC 204). The disappearance of the bis(acyloxymethyl) phosphate was monitored by reversed-phase chromatography on a column of $\mu$ Bondapak-$C_{18}$ (30 cm×4 mm i.d., 10 $\mu$m; Waters Assoc., Milford, Mass.) using solutions of 0.01M potassium phosphate buffer (pH 7.0) with methanol as the mobile phase (typically 25–50% alcohol).

The mechanism for this change is probably as shown below.

(A)

(B)

(C)

(D)         (E)

The bis(acetoxymethyl) phosphate A is solvolyzed to form an intermediate B, which spontaneously eliminates formaldehyde. A mono(acetoxymethyl) phosphate C results, and is further demasked to a next intermediate D and the parent phosphate E by repetition of the same steps. A labile intermediate was detected in some solutions by HPLC, but was not characterized.

The formation of intermediate B and mono(acetoxymethyl) phosphate C was monitored by ion-pair chromatography on $\mu$ Bondapak-C using the same buffer system as described above, except that tetrabutylammonium hydroxide was added to a concentration $2\times 10^{-3}$M, or by anion-exchange chromatography on a column of Partisil SAX (25 cm×4.6 mm i.d., 10 $\mu$m; Whatman) using a linear gradient of 0.01–0.1M potassium phosphate buffer (pH 6.5) as an eluent. The flow rates for these analyses and the ones described above ranged from 1.0 to 2.0 ml/min. The column effluents were monitored at 254 nm with a Schoeffel model 450 UV detector, and the concentrations were determined by comparison of the peak areas with those of reference standards.

When the bis(acetoxymethyl) phenyl phosphate was incubated at a concentration of 65 micrograms per milliliter at 37° C. in 0.05M potassium phosphate buffer (pH 7.4) with either hog liver carboxylate esterase (obtained from Sigma Chemicals, St. Louis, Mo.) (E.C. No. 3.1.1.1., 8 milligrams protein per milliliter) or mouse plasma (50% by volume) it was rapidly degraded, first to the mono(acetoxymethyl) analog, and then to the parent phenyl phosphate. The half-life was less than 15 minutes. (At appropriate intervals, aliquots (100 $\mu$l) of the incubation mixtures were diluted with 3 volumes of methanol and then agitated for 1 minute on a Vortex shaker. The precipitated protein was separated by centrifugation at 10,000×g for 5 minutes, and the supernatants were analyzed by HPLC as described above.)

EXAMPLE 3

In this case iodomethyl pivaloate was used (i.e., $R^1$ was $C(CH_3)_3$). Preparation was otherwise the same as in Example 2. The product, bis(pivaloyloxymethyl) phenyl phosphate, was produced with a 54% yield.

This phosphotriester was much more resistant to both chemical and enzymatic hydrolysis than the protected composition of Example 1. It was stable in protonic solvents and had a half-life of about 5 hours when incubated with mouse plasma under the same conditions as in Example 2. This demonstrates that the acyl substituent has a substantial effect on the rate of hydrolysis.

EXAMPLE 4

Disilverbenzyl phosphate was reacted with iodomethyl pivaloate. The product was bis(pivaloyloxymethyl) benzyl phosphate. Catalytic hydrogenolysis of this product over 5% Pd-C in cyclohexane gave the corresponding monobasic acid. This acid was isolated in its cyclohexyl ammonium salt form.

Successive ion exchange of the salt on Dowex 50 $Na^+$ and Dowex 50 $Ag^+$ produced silver bis(pivaloyloxymethyl) phosphate. This compound is very useful in synthesizing other bis(acyloxymethyl) phosphoesters. For example, when reacted with benzyl bromide or methyl iodide in benzene at room temperature for about 5 hours, the corresponding benzyl and methyl phosphotriesters are produced in nearly quantitative yield.

The synthesis of this example can be summarized as follows:

EXAMPLE 5

The silver diester product of Example 4 was reacted with 5'-deoxy-5'-iodo-3'-O-acetylthymidine, as shown below.

The R substituent shown was a methyl group.

The reaction was carried out under reflux for about 5 hours. Bis(pivaloyloxymethyl) 3'-O-acethythymidine-5'-phosphate was produced in 39% yield.

EXAMPLE 6

Example 5 was repeated with the R substituent changed to fluorine (i.e., 2',5-dideoxy-5'-iodo-3'-O-acetyl-5-fluorouridine). There was a 15% yield of this product. This composition prevented the growth of Chinese hamster ovary cells in culture at a concentration of $5.0 \times 10^{-6} M$ [5-fluoro-2'-deoxyuridine (5-FUdR) control, $1.0 \times 10^{-6} M$].

EXAMPLE 7

Several bis(acyloxymethyl) esters of 5-fluoro-2'-deoxyuridine-5" phosphate (5-FdUMP) were prepared through condensation of 5-FUdR or 3'-O-acetyl-5-FUdR with bis(acyloxymethyl) phosphates. One in particular, 5-FUdR-(3'-OCOCH$_3$)—5'-O-[P(O)(OCH$_2$OCOC(CH$_3$)$_3$)$_2$], was incubated at 3° C. with mouse plasma and hog liver carboxylate esterase. The acyloxymethyl groups and the 3'-acetyl group were successively cleaved to give 5-FdUMP. When the bis(acyloxymethyl) ester was tested, it prevented the growth of Chinese hamster ovary cells in culture at a concentration of $1 \times 10^{-6} M$. It also proved active against P388 leukemia which is resistant to 5-fluorouracil.

Other groups of compounds in accordance with the present invention include the following:

A. Bis(acyloxymethyl) esters of uracil 2',3'-dideoxynucleotides and substituted analogues.

B. Mono(acyloxymethyl) esters of uracil 2',3'-dideoxynucleotides and substituted analogues.

C. Bis(acyloxymethyl) esters of cytosine 2',3'-dideoxynucleotides and substituted analogues.

D. Mono(acyloxymethyl) esters of cytosine 2',3'-dideoxynucleotides and substituted analogues.

E. Mono(acyloxymethyl) esters of purine 2',3'-dideoxynucleotides and substituted analogues.

F. Mono(acyloxymethyl) and bis(acyloxymethyl) esters of pyrimidine acyclic nucleotides.

Such compounds will be discussed in more detail in Examples 8–14.

EXAMPLE 8

Bis(acyloxymethyl) esters of uracil 2',3'-dideoxynucleotides and substituted analogues

I

| Compound | R¹ | R² |
|---|---|---|
| I 1 | (CH₃)₃C | 2',3'-dideoxyuridine-5'-yl |
| I 2 | (CH₃)₂CH | 2',3'-dideoxyuridine-5'-yl |
| I 3 | CH₃CH₂ | 2',3'-dideoxyuridine-5'-yl |
| I 4 | CH₃ | 2',3'-dideoxyuridine-5'-yl |
| I 5 | (CH₃)₃C | 2'-fluoro-2',3'-dideoxyuridine-5'-yl |
| I 6 | (CH₃)₃C | 3'-fluoro-2',3'-dideoxyuridine-5'-yl |
| I 7 | (CH₃)₃C | 3'-azido-2',3'-dideoxyuridine-5'-yl |
| I 8 | (CH₃)₃C | 3'-amino-2',3'-dideoxyuridine-5'-yl |
| I 9 | (CH₃)₃C | 5-chloro-2',3'-dideoxyuridine-5'-yl |
| I 10 | (CH₃)₃C | 5-bromo-2',3'-dideoxyuridine-5'-yl |
| I 11 | (CH₃)₃C | 5-iodo-2',3'-dideoxyuridine-5'-yl |
| I 12 | (CH₃)₃C | 5-methyl-2',3'-dideoxyuridine-5'-yl |
| I 13 | (CH₃)₃C | 5-methyl-3'-fluoro-2',3'-dideoxyuridine-5'-yl |
| I 14 | (CH₃)₃C | 5-methyl-3'-azido-2',3'-dideoxyuridine-5'-yl |
| I 15 | (CH₃)₃C | 5-methyl-3'-amino-2',3'-dideoxyuridine-5'-yl |
| I 16 | (CH₃)₃C | 5-ethyl-2',3'-dideoxyuridine-5'-yl |
| I 17 | (CH₃)₃C | 5-propyl-2',3'-dideoxyuridine-5'-yl |

The starting dideoxynucleotides were prepared as described in P. Herdewijn, J. Balzarini, E. DeClercq, R. Pauwels, B. Masanori, S. Broder, H. Vanderhaeghe, "3'-substituted 2',3'-Dideoxynucleoside Analogs as Potential Anti-HIV (HTLV-III/LAV) Agents," J. Med. Chem. 30, 1270–8 (1987); and references therein. Except for the 3-amino analogues 8 and 16, all of the compounds were synthesized by condensing the parent nucleosides with the appropriate bis(acyloxymethyl) phosphate in dimethylformamide in the presence of triphenylphosphine/diethyl azodicarboxylate as described above; a brief account of the procedure is given below. The 3-amino analogues 8 and 16 were prepared by catalytic reduction of the 3-azido analogues 7 and 15 over Pd/C by conventional hydrogenation techniques. T. A. Krenitsky, G. A. Freeman, S. R. Shaver, et al, "3'-Amino-2',3'-dideoxyribonucleosides of Some Pyrimidines; Synthesis and Biological Activities," J. Med. Chem. 26, 891–895 (1983).

The nucleoside analogue (1.0 mmol), triphenylphosphine (0.60 g, 2.28 mmol) and bis(pivaloyloxymethyl) phosphate (0.5 g, 5.5 mmol) were dissolved in dimethylacetamide (10 mL) contained in a 15 mL round-bottom flask. A solution of diethyl azodicarboxylate (0.40 g, 2.29 mmol) in dimethylacetamide (2 mL) was added dropwise over 30 minutes, and the mixture was allowed to stir for 3 days at ambient temperature. The solution was evaporated in vacuo then the residue was taken up in chloroform, filtered, and chromatographed on a column of silica (Merck, 230–400 mesh; ca. 10 g) using ethyl acetate/hexane (typically 70:30) as eluent. Fractions of 5 mL were collected. Aliquots of each fraction were analyzed by ascending TLC on silica-coated glass plates (silica gel 60 F 254, Merck) using CHCl₃-MeOH (typically 1–10% MeOH) as the eluting solvent. Chromatograms were visualized under a UV lamp (254 nm). Compounds containing an acyloxymethyl group were identified by spraying the plates with a 0.25% solution of Purpald in 0.5 N NaOH solution and heating in an oven at 85° C. for 5 min. The formaldehyde liberated from the acyloxymethyl groups reacted with the spray reagent to form purple spots against a white background.

All of the products were obtained as viscous colorless oils.

EXAMPLE 9

Mono(acyloxymethyl) esters of uracil 2',3'-dideoxynucleotides and substituted analogues

II

| Compound | R¹ | R² |
|---|---|---|
| II 1 | (CH₃)₃C | 2',3'-dideoxyuridine-5'-yl |
| II 2 | (CH₃)₂CH | 2',3'-dideoxyuridine-5'-yl |
| II 3 | CH₃CH₂ | 2',3'-dideoxyuridine-5'-yl |
| II 4 | CH₃ | 2',3'-dideoxyuridine-5'-yl |
| II 5 | (CH₃)₃C | 2'-fluoro-2',3'-dideoxyuridine-5'-yl |
| II 6 | (CH₃)₃C | 3'-fluoro-2',3'-dideoxyuridine-5'-yl |
| II 7 | (CH₃)₃C | 3'-azido-2',3'-dideoxyuridine-5'-yl |
| II 8 | (CH₃)₃C | 3'-amino-2',3'-dideoxyuridine-5'-yl |
| II 9 | (CH₃)₃C | 5-chloro-2',3'-dideoxyuridine-5'-yl |
| II 10 | (CH₃)₃C | 5-bromo-2',3'-dideoxyuridine-5'-yl |
| II 11 | (CH₃)₃C | 5-iodo-2',3'-dideoxyuridine-5'-yl |
| II 12 | (CH₃)₃C | 5-methyl-2',3'-dideoxyuridine-5'-yl |
| II 13 | (CH₃)₃C | 5-methyl-3'-fluoro-2',3'-dideoxyuridine-5'-yl |
| II 14 | (CH₃)₃C | 5-methyl-3'-azido-2',3'-dideoxyuridine-5'-yl |
| II 15 | (CH₃)₃C | 5-methyl-3'-amino-2',3'-dideoxyuridine-5'-yl |
| II 16 | (CH₃)₃C | 5-ethyl-2',3'-dideoxyuridine-5'-yl |
| II 17 | (CH₃)₃C | 5-propyl-2',3'-dideoxyuridine-5'-yl |

All of the compounds except for 8 and 16 were prepared form theparent nucleosides by condensation with mono(pivaloyloxymethyl) phosphate in pyridine in the presence of dicyclohexylcarbodiimide as described below. Compounds 8 and 16 were prepared by catalytic reduction of the 3-azido analogues 7 and 15 over Pd/C. T. A. Krenitsky, G. A. Freeman, S. R. Shaver, et al., "3'-Amino-2',3'-dideoxyribonucleosides of some Pyrimidines; Synthesis and Biological Activities," J. Med. Chem. 26, 891–895 (1983).

The nucleoside (1 mmol) was dried by repeated evaporation from pyridine (5×5 mL). It was then taken up in pyridine (5 mL) and the solution was cooled to 5° C. Monopivaloyloxymethyl phosphate (0.25 g, 1.2 mmol) was added followed by dicyclohexylcarbodiimide (0.25 g, 1.2 mmol). The reaction mixture was stirred at room temperature for 3 days then concentrated in vacuo at <30° C. to remove pyridine. Water (5.0 mL) was added then the solution was adjusted to pH 7.0 with acetic acid. The mixture was stirred for 10 minutes then the precipitated dicyclohexylurea was filtered off. The filtrate was passed through a column of Dowex 50 cation-exchange resin in the H⁺ form and the eluent was immediately frozen and lyophilized. The residual gum was purified by chromatography on a thick layer of silica (20 cm×20 cm×2 mm) using chloroform-methanol (typically 3:1) as eluent. The products were isolated as viscous colorless oils.

EXAMPLE 10

Bis(acyloxymethyl) esters of cytosine 2',3'-dideoxynucleotides and substituted analogues

| Compound | R¹ | R² |
|---|---|---|
| III 1 | (CH₃)₃C | 2',3'-dideoxycytidin-5'-yl |
| III 2 | (CH₃)₃C | 2'-fluoro-2',3'-dideoxycytidin-5'-yl |
| III 3 | (CH₃)₃C | 3'-fluoro-2',3'-dideoxycytidin-5'-yl |
| III 4 | (CH₃)₃C | 3'-azido-2',3'-dideoxycytidin-5'-yl |
| III 5 | (CH₃)₃C | 5-fluoro-2',3'-dideoxycytidin-5'-yl |
| III 6 | (CH₃)₃C | 5-chloro-2',3'-dideoxycytidin-5'-yl |
| III 7 | (CH₃)₃C | 5-bromo-2',3'-dideoxycytidin-5'-yl |
| III 8 | (CH₃)₃C | 5-iodo-2',3'-dideoxycytidin-5'-yl |
| III 9 | (CH₃)₃C | 5-methyl-2',3'-dideoxycytidin-5'-yl |
| III 10 | (CH₃)₃C | 5-methyl-3'-fluoro-2',3'-dideoxycytidin-5'-yl |
| III 11 | (CH₃)₃C | 5-methyl-3'-azido-2',3'-dideoxycytidin-5'-yl |

These dideoxycytidine nucleotide esters were prepared by coupling the parent N-carbobenzyloxy nucleoside with bis(pivaloyloxymethyl) phosphate in the presence of triphenyl phosphine and diethyl azodicarboxylate as described for the uracil analogues, I, above. The 4-amino groups were protected as their N-carbobenzyloxy derivatives as described for cytidine. K. Kondo, T. Nagara et al, "Studies on Biologically Active Nucleosides and Nucleotides, Part. 5," J. Med. Chem. 22, 639–646 (1979). When the coupling reaction was complete, the N-carbobenzyloxy protective groups were removed by hydrogenation over 5% palladium-on-charcoal in ethanol. The final products were isolated as the corresponding hydrochloride salts by treating a 10% solution of the free base in chloroform with an excess of a 5% solution of hydrogen chloride in ether. The precipitated hydrochlorides were filtered and dried under vacuum over P₂O₅. For compound 7, the trichloroethoxycarbonyl protective group was used instead of the benzyloxycarbonyl group; it was removed with Zn/Cu in DMF as described in F. Eckstein, "The Trichloroethyl Group as a Protecting Group for Phosphate in the Synthesis of Mononucleotides," Angew. Chem. (Ger.) 77, 912 (1965).

EXAMPLE 11

Mono(acyloxymethyl) esters of cytosine 2',3'-dideoxynucleotides and substituted analogues

| Compound | R¹ | R² |
|---|---|---|
| IV 1 | (CH₃)₃C | 2',3'-dideoxycytidin-5'-yl |
| IV 2 | (CH₃)₃C | 2'-fluoro-2',3'-dideoxycytidin-5'-yl |
| IV 3 | (CH₃)₃C | 3'-fluoro-2',3'-dideoxycytidin-5'-yl |
| IV 4 | (CH₃)₃C | 3'-azido-2',3'-dideoxycytidin-5'-yl |
| IV 5 | (CH₃)₃C | 5-fluoro-2',3'-dideoxycytidin-5'-yl |
| IV 6 | (CH₃)₃C | 5-chloro-2',3'-dideoxycytidin-5'-yl |

| Compound | R¹ | R² |
|---|---|---|
| IV 7 | (CH₃)₃C | 5-bromo-2',3'-dideoxycytidin-5'-yl |
| IV 8 | (CH₃)₃C | 5-iodo-2',3'-dideoxycytidin-5'-yl |
| IV 9 | (CH₃)₃C | 5-methyl-2',3'-dideoxycytidin-5'-yl |
| IV 10 | (CH₃)₃C | 5-methyl-3'-fluoro-2',3'-dideoxycytidin-5'-yl |
| IV 11 | (CH₃)₃C | 5-methyl-3'-azido-2',3'-dideoxycytidin-5'-yl |

These diesters were prepared from the parent N-benzyloxycarbonyl nucleosides by condensation with monopivaloyloxymethyl phosphate in pyridine as solvent in the presence of dicyclohexylcarbodiimide as described above for the uracil analogues II. In the final step the benzyloxycarbonyl protective groups were removed as usual by a catalytic hydrogenation over 5% palladium-on-charcoal.

EXAMPLE 12

Mono(acyloxymethyl) esters of purine 2',3'-dideoxynucleotides

| Compound | R¹ | R² |
|---|---|---|
| V 1 | (CH₃)₃C | 2',3'-dideoxyadenosin-5'-yl |
| V 2 | (CH₃)₃C | 2',3'-dideoxyguanosin-5'-yl |
| V 3 | (CH₃)₃C | 2',3'-dideoxyxanthosin-5'-yl |

These compounds were prepared by reaction of the nucleoside analogue with mono(pivaloyloxymethyl) phosphate in pyridine as solvent in the presence of 2,4,6-triisopropylbenzenesulfonyl tetrazole as condensing agent by the general procedure described by D. E. Gibbs and L. E Orgel, "Some 5'-Azido and 5'-amino-2'-deoxyribonucleosides, their 3'-phosphates, and their 3'-phosphoimidazolides," J. Carbohydrates, Nucleosides and Nucleotides, 3, 315–334 (1976).

EXAMPLE 13

Mono(acyloxymethyl) and bis(acyloxymethyl) esters of pyrimidine acyclic nucleotides

These compounds were prepared from the patent, from acyclic nucleotides (E. DeClercq and R. T. Walker, "Chemotherapeutic Agents for Herpesvirus Infections," Progress in Medicinal Chemistry, 23, 187–218 (1986); and references therein, and M. Mansuri and J. C. Martin, Annual) Reviews in Medicinal Chemistry: Antiviral Agents, 22, 139–148 (1987); and references therein) by condensation with bis(acyloxymethyl) phosphate or mono(acyloxymethyl) phosphate by the general procedures described above for the uracil (I) and cytosine (III) analogues.

| Compound | $R^1$ | Base |
|---|---|---|
| VI 1 | $(CH_3)_3C$ | Thymine |
| VI 2 | $(CH_3)_3C$ | Uracil |
| VI 3 | $(CH_3)_3C$ | Cytosine |

EXAMPLE 14

Mono(acyloxymethyl) esters of pyrimidine and purine acyclic nucleotides

VII

| Compound | $R^1$ | Base |
|---|---|---|
| VII 1 | $(CH_3)_3C$ | Guanine |
| VII 2 | $(CH_3)_3C$ | Adenine |
| VII 3 | $(CH_3)_3C$ | Thymine |
| VII 4 | $(CH_3)_3C$ | Uracil |
| VII 5 | $(CH_3)_3C$ | Cytosine |
| VII 6 | $(CH_3)_3C$ | Xanthine |

These compounds were prepared from the parent free acyclic nucleotides by condensation with bis(acyloxymethyl) phosphate or mono(acyloxymethyl) phosphate as described above for the uracil (II), cytosine (IV), and purine (V) analogues.

Testing of these compounds has confirmed that the protective groups are removed under the appropriate conditions. Some of the compounds have been tested for biological activity, and have shown positive results.

Methods in accordance with the present invention comprise administering to a mammal an effective amount of one or more of the compounds described above. The administering step is preferably by intravenous, intraarterial, intramuscular, intralymphatic, intraperitoneal, subcutaneous, intrapleural or intrathecal injection or by topical application or oral dosage.

The preceding examples and description are intended to be illustrative, but not to limit the scope of the invention. Those skilled in the art will appreciate that the present invention has a number of potential applications and a variety of possible embodiments.

What is claimed is:

1. Compounds having the formula where
$R^1$ is selected from the group consisting of H, alkyl hydrocarbons having 1–10 carbons, aryl and alkaryl hydrocarbons having 6–10 carbons, and amines having the formula $NR^4R^5$, where $R^4$ and $R^5$ are independently selected from the group consisting of H and alkyl hydrocarbons having 1–10 carbons;
$R^3$ is selected from the group consisting of H and alkyl hydrocarbons having 1–3 carbons;
$X^1$ is selected from the group consisting of H and
$X^2$ is selected from the group consisting of $R^2$ and $OR^2$; and
$R^2$ is selected from the group consisting of H, alkyl hydrocarbons having 1–10 carbons, aryl and alkaryl hydrocarbons having 6–10 carbons, and nucleosides.

2. The compounds of claim 1, where $R^1$ is selected from the group consisting of H, $CH_3$, $CH_2CH_3$, $CH(CH_3)_2$, and $C(CH_3)_3$.

3. The compounds of claim 1, where $R^3$ is H.

4. The compounds of claim 1, where $R^2$ is selected from the group consisting of
uracil 2',3'-dideoxynucleosides,
cytosine 2',3'-dideoxynucleosides,
purine 2',3'-dideoxynucleosides, and
pyrimidine acyclic nucleosides.

5. The compounds of claim 1, where $R^2$ is selected from the group consisting of
2',3'-dideoxyuridin-5'-yl groups
2',3'-dideoxycytidin-5'-yl groups
2',3'-dideoxyguanosin-5'-yl groups,
and groups having the formula

$CH_2CH_2OCH_2B$ where B is a base selected from the group consisting of thymine, uracil, cytosine, guanine, adenine, and xanthine.

6. The compounds of claim 1, where $R^2$ is selected from the, group consisting of
2',3'-dideoxyuridine-5'-yl
2'-fluoro-2',3'-dideoxyuridine-5'-yl
3'-fluoro-2',3'-dideoxyuridine-5'-yl
3'-azido-2',3'-dideoxyuridine-5'-yl
3'-amino-2',3'-dideoxyuridine-5'-yl
5-chloro-2',3'-dideoxyuridine-5'-yl
5-bromo-2',3'-dideoxyuridine-5'-yl
5-iodo-2',3'-dideoxyuridine-5'-yl
5-methyl-2',3'-dideoxyuridine-5'-yl
5-methyl-3'-fluoro-2',3'-dideoxyuridine-5'-yl
5-methyl-3'-azido-2',3'-dideoxyuridine-5'-yl
5-methyl-3'-amino-2',3'-dideoxyuridine-5'-yl
5-ethyl-2',3'-dideoxyuridine-5'-yl
5'-propyl-2',3'-dideoxyuridine-5'-yl
2',3'-dideoxycytidin-5'-yl
2'-fluoro-2',3'-dideoxycytidin-5'-yl
3'-fluoro-2',3'-dideoxycytidin-5'-yl
3'-azido-2',3'-dideoxycytidin-5'-yl
5-fluoro-2',3'-dideoxycytidin-5'-yl
5-chloro-2',3'-dideoxycytidin-5'-yl
5-bromo-2',3'-dideoxyctidin-5'-yl
5-iodo-2',3'-dideoxycytidin-5'-yl
5-methyl-2',3'-dideoxycytidin-5'-yl
5-methyl-3'-fluoro-2',3'-dideoxycytidin-5'-yl
5-methyl-3'-azido-2',3'-dideoxycytidin-5'-yl
2',3'-dideoxyadenosin-5'-yl
2',3'-dideoxyguanosin-5'-yl
2',3'-dideoxyxanthosin-5'-yl
—$CH_2CH_2OCH_2$—Guanine
—$CH_2CH_2OCH_2$—Adenine
—$CH_2CH_2OCH_2$—Thymine
—$CH_2CH_2OCH_2$—Uracil
—$CH_2CH_2OCH_2$—Cytosine —CH₂CH₂OCH₂—Xanthine.

7. Compounds having the formula where
R¹ is selected from the group consisting of CH₃, CH₂CH₃, CH(CH₃)₂, and C(CH₃)₃;
X¹ selected from the group consisting of H and R¹COOCH₂; and
R² is selected from the group consisting of
2′,3′-dideoxyuridin-5′-yl groups
2′,3′-dideoxycytidin-5′-yl groups
2′,3′-dideoxyguanosin-5′-yl groups,
and groups having the formula

CH₂CH₂OCH₂B where B is a base selected from the group consisting of thymine, uracil, cytosine, guanine, adenine, and xanthine.

8. Compounds having the formula where
R¹ is selected from the group consisting of H, CH₃, CH₂CH₃, CH(CH₃)₂, and C(CH₃)₃; and
R² is selected from the group consisting of
2′,3′-dideoxyuridine-5′-yl
2′-fluoro-2′,3′-dideoxyuridine-5′-yl
3′-fluoro-2′,3′-dideoxyuridine-5′-yl
3′-azido-2′,3′-dideoxyuridine-5′-yl
3′-amino-2′,3′-dideoxyuridine-5′-yl
5-chloro-2′,3′-dideoxyuridine-5′-yl
5-bromo-2′,3′-dideoxyuridine-5′-yl
5-iodo-2′,3′-dideoxyuridine-5′-yl
5-methyl-2′,3′-dideoxyuridine-5′-yl
5-methyl-3′-fluoro-2′,3′-diideoxyuridine-5′-yl
5-methyl-3′-azido-2′,3′-dideoxyuridine-5′-yl
5-methyl-3′-amino-2′,3′-dideoxyuridine-5′-yl
5-ethyl-2′,3′-dideoxyuridine-5′-yl
5-propyl-2′,3′-dideoxyuridine-5′-yl
2′,3′-dideoxycytidin-5′-yl
2′-fluoro-2′,3′-dideoxycytidin-5′-yl
3′-fluoro-2′,3′-dideoxycytidin-5′-yl
3′-azido-2′,3′-dideoxycytidin-5′-yl
5-fluoro-2′,3′-dideoxycytidin-5′-yl
5-chloro-2′,3′-dideoxycytidin-5′-yl
5-bromo-2′,3′-dideoxycytidin-5′-yl
5-iodo-2′,3′-dideoxycytidin-5′-yl
5-methyl-2′,3′-dideoxycytidin-5′-yl
5-methyl-3′-fluoro-2′,3′-dideoxycytidin-5′-yl
5-methyl-3′-azido-2′,3′-dideoxycytidin-5′-yl
2′,3′-dideoxyadenosin-5′-yl
2′,3′-dideoxyguanosin-5′-yl
2′,3′-dideoxyxanthosin-5′-yl

—CH₂CH₂OCH₂—Guanine
—CH₂CH₂OCH₂—Adenine
—CH₂CH₂OCH₂—Thymine
—CH₂CH₂OCH₂—Uracil
—CH₂CH₂OCH₂—Cytosine
—CH₂CH₂OCH₂—Xanthine 9. Compounds having the formula where
R¹ is selected from the group consisting of H, CH₃, CH₂CH₃, CH(CH₃)₂, and C(CH₃)₃; and
R² is selected from the group consisting of
2′,3′-dideoxyuridine-5′-yl
2′fluoro-2′,3′-dideoxyuridine-5′-yl;
3′-fluoro-2′,3′-dideoxyuridine-5′-yl
3′-azido-2′,3′-dideoxyuridine-5′-yl
3′-amino-2′,3′-dideoxyuridine-5′-yl
5-chloro-2′,3′-dideoxyuridine-5′-yl
5-bromo-2′,3′-dideoxyuridine-5′-yl
5-iodo-2′,3′-dideoxyuridine-5′-yl
5-methyl-2′,3′-dideoxyuridine-5′-yl
5-methyl-3′-fluoro-2′,3′-dideoxyuridine-5′-yl
5-methyl-3′-azido-2′,3′-dideoxyuridine-5′-yl
5-methyl-3′-amino-2′,3′-dideoxyuridine-5′-yl
5-ethyl-2′,3′-dideoxyuridine-5′-yl
5-propyl-2′,3′-dideoxyuridine-5′-yl
2′,3′-dideoxycytidin-5′-yl
2′-fluoro-2′,3′-diedoxycytidin-5′-yl
3′-fluoro-2′,3′-dideoxycytidin-5′-yl
3′-azido-2′,3′-dideoxycytidin-5′-yl
5-fluoro-2′,3′-dideoxycytidin-5′-yl
5-chloro-2′,3′-dideoxycytidin-5′-yl
5-bromo-2′,3′-dideoxycytidin-5′-yl
5-iodo-2′,3′-dideoxycytidin-5′-yl
5-methyl-2′,3′-dideoxycytidin-5′-yl
5-methyl-3′-fluoro-2′,3′-dideoxycytidin-5′-yl
5-methy-3′-azido-2′,3′-dideoxycytidin-5′-yl
2′,3′-dideoxyadenosin-5′-yl
2′,3′-dideoxyguanosin-5′-yl
2′,3′-dideoxyxanthosin-5′-yl
—CH₂CH₂OCH₂—Guanine
—CH₂CH₂OCH₂—Adenine
—CH₂CH₂OCH₂—Thymine
—CH₂CH₂OCH₂—Uracil
—CH₂CH₂OCH₂—Cytosine
—CH₂CH₂OCH₂—Xanthine.

10. Compounds having the formula where
R¹ is selected from the group consisting of H, CH₃, CH₂CH₃, CH(CH₃)₂, and C(CH₃)₃; and
R² is selected from the group consisting of
2′,3′-dideoxyuridine-5′-yl

2'-fluoro-2',3'-dideoxyuridine-5'-yl
3'-fluoro-2',3'-dideoxyuridine-5'-yl
3'-azido-2',3'-dideoxyuridine-5'-yl
3'amino-2',3'-didoxyuridine-5'-yl
5-chloro-2',3'-dideoxyuridine-5'-yl
5-bromo-2,3'-dideoxyuridine-5'-yl
5-iodo-2',3'-dideoxyuridine-5'-yl
5-methyl-2',3'-dideoxyuridine-5'-yl
5-methyl-3'-fluoro-2',3'-dideoxyuridine-5'-yl
5-methyl-3'-azido-2',3'-dideoxyuridine-5'-yl
5-methyl-3'-amino-2',3'-dideoxyuridine-5'-yl
5-ethyl-2',3'-dideoxyuridine-5'-yl
5-propyl-2',3'-dideoxyuridine-5'-yl
2',3'-dideoxycytidin-5'-yl
2'-fluoro-2',3'-dideoxycytidin-5'-yl
3'-fluoro-2',3'-dideoxycytidin-5'-yl
3'-azido-2',3'-dideoxycytidin-5'-yl
5-fluoro-2',3'-dideoxycytidin-5'-yl
5-chloro-2',3'-dideoxycytidin-5'-yl
5-bromo-2',3'-dideoxycytidin-5'-yl
5-iodo-2',3'-dideoxycytidin-5'-yl
5-methyl-2',3'-dideoxycytidin-5'-yl
5-methyl-3'-fluoro-2',3'-dideoxycytidin-5'-yl
5-methyl-3'-azido-2',3'-dideoxycytidin-5'-yl.

11. Compounds having the formula where
R$^1$ is selected from the group consisting of H, CH$_3$, CH$_2$CH$_3$, CH(CH$_3$)$_2$, and C(CH$_3$)$_3$; and
R$^2$ is selected from the group consisting of
2',3'-dideoxyuridine-5'-yl
2'-fluoro-2',3'-dideoxyuridine-5'-yl
3'-fluoro-2',3'-dideoxyuridine-5'-yl
3'-azido-2',3'-dideoxyuridine-5'-yl
3'-amino-2',3'-dideoxyuridine-5'-yl
5-chloro-2',3'-dideoxyuridine-5'-yl
5-bromo-2,3'-dideoxyuridine-5'-yl
5-iodo-2',3'-dideoxyuridine-5'-yl
5-methyl-2',3'-dideoxyuridine-5'-yl
5-methyl-3'-fluoro-2',3'-dideoxyuridine-5'-yl
5-methyl-3'-azido-2',3'-dideoxyuridine-5'-yl
5-methyl-3'-amino-2',3'-dideoxyuridine-5'-yl
5-ethyl-2',3'-dideoxyuridine-5'-yl
5-propyl-2',3'-dideoxyuridine-5'-yl
2',3'-dideoxycytidin-5'-yl
2'-fluoro-2',3'-dideoxycytidin-5'-yl
3'-fluoro-2',3'-dideoxycytidin-5'-yl
3'-azido-2',3'-dideoxycytidin-5'-yl
5-fluoro-2',3'-dideoxycytidin-5'-yl
5-chloro-2',3'-dideoxycytidin-5'-yl
5-bromo-2',3'-dideoxycytidin-5'-yl
5-iodo-2',3'-dideoxycytidin-5'-yl
5-methyl-2',3'-dideoxycytidin-5'-yl
5-methyl-3'-fluoro-2',3'-dideoxycytidin-5'-yl
5-methyl-3'-azido-2',3'-dideoxycytidin-5'-yl.

12. Compounds having the formula where
R$^1$ is selected from the group consisting of H, CH$_3$, CH$_2$CH$_3$, CH(CH$_3$)$_2$, and C(CH$_3$)$_3$; and
R$^2$ is selected from the group consisting of
2',3'-dideoxyadensosin-5'-yl, and
2',3'-dideoxyxanthosin-5'-yl.
2',3'-dideoxyxanthosin-5'-yl.

13. Compounds having the formula where
R$^1$ is selected from the group consisting of H, CH$_3$, CH$_2$CH$_3$, CH(CH$_3$)$_2$, and C(CH$_3$)$_3$; and
B is a base selected from the group consisting of guanine, adenine, thymine, uracil, cytosine, and xanthine.

14. Compounds having the formula where
R$^1$ is selected from the group consisting of H, CH$_3$, CH$_2$CH$_3$, CH(CH$_3$)$_2$, and C(CH$_3$)$_3$; and
B is a base selected from the group consisting of guanine, adenine, thymine, uracil, cytosine, and xanthine.

* * * * *

UNITED STATES PATENT AND TRADEMARK OFFICE
CERTIFICATE OF CORRECTION

PATENT NO. : 4,968,788
DATED : Nov. 6, 1990
INVENTOR(S) : David Farquhar

It is certified that error appears in the above-identified patent and that said Letters Patent is hereby corrected as shown below:

In column 14, line 63, "patent," should be --parent--.

In column 14, line 64, "from" should be --free--.

In column 16, line 5, after the word "and", there should appear --$R^1COOCR_2^3$--.

In column 20, line 23, "and" should be deleted.

In column 20, line 24, "2',3'-dideoxyxanthosin-5'-yl." should be --2',3'-dideoxyguanosin-5'-yl, and--.

Signed and Sealed this

Twenty-eighth Day of April, 1992

Attest:

HARRY F. MANBECK, JR.

*Attesting Officer*                *Commissioner of Patents and Trademarks*

UNITED STATES PATENT AND TRADEMARK OFFICE
CERTIFICATE OF CORRECTION

PATENT NO. : 4,968,788
DATED : November 6, 1990
INVENTOR(S) : David Farquhar

It is certified that error appears in the above-identified patent and that said Letters Patent is hereby corrected as shown below:

Column 1, line 4, insert -- This invention was made with government support under Grant No. R01 CA28001 awarded by the National Institutes of Health. The government has certain rights in the invention.--

Signed and Sealed this

Ninth Day of February, 1993

Attest:

STEPHEN G. KUNIN

*Attesting Officer*  *Acting Commissioner of Patents and Trademarks*